United States Patent [19]

Präve et al.

[11] 4,166,004
[45] Aug. 28, 1979

[54] **PROCESS FOR THE PREPARATION OF SINGLE CELL PROTEIN USING *METHYLMONAS CLARA* ATCC 31226**

[75] Inventors: Paul Präve, Bad Soden am Taunus; Dieter Sukatsch, Frankfurt am Main; Uwe Faust, Kelkheim, all of Fed. Rep. of Germany

[73] Assignee: Hoechst Aktiengesellschaft, Frankfurt am Main, Fed. Rep. of Germany

[21] Appl. No.: 817,870

[22] Filed: Jul. 21, 1977

[30] Foreign Application Priority Data

Jul. 24, 1976 [DE] Fed. Rep. of Germany ....... 2633451

[51] Int. Cl.$^2$ ............................................. C12B 1/00
[52] U.S. Cl. .................................... 435/253; 435/804; 435/822
[58] Field of Search ........................... 195/49, 96, 115

[56] References Cited

U.S. PATENT DOCUMENTS

| 3,994,781 | 11/1976 | Thorstendotter ...................... 195/49 |
| 4,006,058 | 2/1977 | Sauins ..................................... 195/49 |
| 4,048,013 | 9/1977 | Wagner et al. ......................... 195/49 |

FOREIGN PATENT DOCUMENTS

| 51-19184 | 2/1976 | Japan ......................................... 195/49 |
| 51-54987 | 5/1976 | Japan ......................................... 195/49 |
| 1420264 | 1/1976 | United Kingdom ...................... 195/49 |
| 1420455 | 1/1976 | United Kingdom ...................... 195/49 |

OTHER PUBLICATIONS

Dostalek et al., "Optimization of Biomass From Methanol", *Proc. IV. IES: Ferment Technol. Today* pp. 497-501 (1972).

*Primary Examiner*—Thomas G. Wiseman
*Attorney, Agent, or Firm*—Curtis, Morris & Safford

[57] ABSTRACT

A process for the preparation of a biomass is disclosed by cultivation of bacteria of the genus Methylomonas under aerobic conditions in a nutrient medium containing methanol as the sole carbon source, nitrogen sources and essential mineral salts, which comprises using a strain of the species *Methylomonas clara* ATCC 31226. The single cell protein thus obtained has a low content of nucleic acids, fats and carbohydrates and is especially suitable to prepare food and feed.

2 Claims, No Drawings

PROCESS FOR THE PREPARATION OF SINGLE CELL PROTEIN USING *METHYLMONAS CLARA* ATCC 31226

The present invention relates to a process for the preparation of single cell protein (biomass) having a high portion of protein and containing moreover fats, carbohydrates and vitamins. The biomass serves as basic material for the preparation of human food and animal feed.

Known processes for the preparation of biomass by means of strains of bacteria, which grow on methanol as the only source of carbon, frequently result in products containing pigments, biopolymers or undesired metabolites such as polyhydroxybutyric acid and thus, they are suitable as foodstuffs for humans and animals to a very limited degree only. The odor, the flavor or the toxic properties of such accompanying substances may even exclude the intended use of the biomass.

A novel strain of bacteria of the genus Methylomonas has now been found which is capable of utilizing methanol, methane or dimethylamine as sole source of carbon. This strain has been designated *Methylamonas clara* FH-B-5460 and is on deposit at the American Type Culture Collection under ATCC 31226.

The process for the preparation of a biomass (single cell protein) according to the invention by cultivating bacteria of the genus Methylomonas under aerobic conditions in a nutrient medium containing methanol as source of carbon, nitrogen sources and mineral salts, comprises using a strain of bacteria of the genus *Methylomonas clara* and maintaining the methanol concentration in a range between 5 and 150 ppm, calculated on the weight of the nutrient medium. Methanol is the sole source of carbon.

Preference is given to a methanol conentration in the range of from 5 to 100 ppm and, for continuous operation, a concentration in the range of from 5 to 30 ppm is particularly preferred.

The process is carried out in well aerated fermenters which hold a nutrient medium comprising in addition to methanol as the sole carbon source salts such as potassium nitrate, ammonium sulfate, ammonium phosphate or ammonia as nitrogen source. It moreover contains phosphates, for example potassium dihydrogen phosphate or disodium hydrogenphosphate and magnesium and potassium salts and finally trace elements which can be found in tap water, especially iron, copper and molybdenum salts.

The process is advantageously carried out at a temperature in the range of from 30° to 42° C., preferably of from 35° to 39° C.

The process according to the invention may be carried out in known fermentation vessels, for example in aerated agitator vessels or in modern fermenters such, for example, as loop reactors, in continuous or in discontinuous operation.

The liquid nutrient medium in the fermenter is aerated with 0.1 to 1.5 liters of air per liter of nutrient medium and minute (vvm).

The methanol concentration to be maintained can be controlled continuously by various measures, for example by measuring the nitrogen consumption, the portion of biomass in the suspension or preferably by measuring the carbon dioxide release. Using the latter method, a quick reaction to the lack of carbon, indicated by a decreasing $CO_2$ release, is possible, and thus the amount of methanol to be added can be calculated accurately. Alternatively the methanol concentration control can be carried out especially advantageously by measuring the gaseous methanol by means of a flame ionization detector.

The pH of the culture suspension consisting of the nutrient medium and the growing cell mass ranges between 4.0 and 9.0, preferably between 6.0 and 7.2. If the pH of the culture suspension falls below the required value, it may be readjusted by the addition of an adequate quantity of alkali metal, for example of sodium hydroxide or of potassium hydroxide solution. Similarily, a too high pH may be readjusted by the addition of acids, for example, of hydrochloric acid or sulfuric acid.

The biomass is separated in usual manner, for example by centrifugation while repeatedly washing with water, using optionally decantors and separators. Thus there is obtained a pasty biomass containing of from 75 to 90% by weight of water.

Drying can be carried out in various ways, for example by means of drum dryers, fluidized bed dryers or spray dryers. The product thus obtained contains only from 1 to 4% by weight of water and of from 80 to 90% by weight of crude protein. This crude protein has a content of amino acids ranging between 75 and 78% by weight, the portion of essential amino acids amounting to about 50% by weight of the total content of amino acids. The product has a low content of nucleic acid, fats and carbohydrates, the content of nucleic acid ranging between about 10 and 14% by weight, of fats between about 5 and 10% by weight and of carbohydrates between about 5 and 10% by weight.

The biomass (single cell protein) thus obtained contains no pigments, no toxic substances, no reserve substances such as biopolymers, no polyhydroxybutyric acid, unwanted odorants or secondary metabolites.

The dried biomass obtained according to the invention is therefore especially suitable as protein source for the preparation of human food and animal feed.

The novel species *Methylomonas clara* FH-B-5460 ATCC 31226 is characterized as follows:

I. Growth attitude:

| | |
|---|---|
| (a) no growth on: | glucose agar or glucose medium, bouillon agar or bouillon nutrient medium, gelatin, peptone agar or medium, litmus milk, potato nutrient medium, amino acid nutrient medium. |
| (b) growth on: | methanol-containing synthetic nutrient medium. |

II. Morphology:

(a) small rods of 0.5 to 1.5 μ, motile by means of polar flagella, no spores, no cysts.
(b) circular colonies, transparent, slightly vitreous.
(c) no pigments.

III. Physiology:

| | |
|---|---|
| (a) growth at: | 20° C. ± |
| | 25° C. + |
| | 30° C. ++ |
| | 35° C. +++ |
| | 37° C. ++++ |
| | 39° C. +++ |
| | 41° C. + |
| optimum growth temperature: | 37° C. |
| optimum pH value: | 6.8 to 7.0 |
| gram negative. | |
| (b) growth factors | not required |
| formation of polyhydroxybutyric acid | − |
| formation of indoles | − |
| formation of acetone | − |
| reduction of $NO_3$ | + |

| -continued | |
|---|---|
| cytochromoxidase | + |
| catalase | + |
| isocitrate dehydrogenase | + |
| malate dehydrogenase | + |
| oxidase | + |
| formation of $H_2S$ | − |
| liquefaction of gelatine | − |
| hydrolysis of starch | − |
| formatin of citric acid | − |
| coagulation of milk | − |
| Growth on | |
| ammonium salts | + |
| ureas | − |
| acetate | − |
| dimethylamine | + |
| trimethylamine | − |
| monomethylamine | − |
| formiate | − |
| formaldehyde | − |
| sugar, polysaccharides | − |
| alcohols (except methanol) | − |
| fixation of $N_2$ | + |
| fixation of $CO_2$ | |

Several known species of Methylomonas and other methanol utilizing microorganisms are described in Bergey's Manual of Determinative Bacteriology, 8th edition, the Williams & Wilkens Company, Baltimore, 1974. Further, related strains are disclosed in various publications. The characteristic properties of the novel species *Methylomonas clara*, in comparison with that of known species, are given in the following Table 1. It can be seen from the table that the Pseudomonas species differ from the novel species in that they form polyhydroxybutyric acid and in that they do not grow on methane or dimethylamine. The known Methylomonas species differ from the novel species by their temperature optimum, the formation of pigments, the formation of polyhydroxybutyric acid and by their coccal form. A further important difference between the novel species and the known species is the hexulose phosphate pathway. This pathway is energetically favored in the case of the novel species in comparison with the serine pathway in the course of the methanol utilization.

In the following table the symbol G+ G(%) at the bottom of the first column indicates the guanine and the cytosine portion of the total content of the pyrimidine bases.

In column 2 there is characterized the novel species *Methylomonas clara* ATCC 31226.

Columns 3 to 7 and column 11 show related strains, which are described in Bergey's Manual of Determinative Bacteriolog, 8th edition, 1974, The Williams & Wilkens Company/Baltimore.

Column 8 to 11 show related species selected from various publications, namely *Pseudomonas methanolica*, disclosed in U.S. Pat. No. 3,755,082; Pseudomonas AM 1, disclosed in J. Bact. 114 (1), 390 (1973); *Pseudomonas methylotropa*, disclosed in German Offenlegungsschrift No. 2,261,164.

Table 1

| | Methylomonas clara FH-B-5460 ATCC 31226 | Methylomonas methanica | Methylomonas methanooxidans | Methylomonas methanonitrificans | Methylococcus capsalaticus |
|---|---|---|---|---|---|
| single cell shape[micron] | 0.5 × 1.5 rods | 0.6 × 1.0 rods | 1 × 3 rods | 1 × 2<br>2 × 4 rods | 1 × 1 cocci |
| motility | + | | + | + | − |
| formation of pigments | − | + | − | + | − |
| pHBS | − | − | − | + | − |
| fixation of $N_2$ | + | − | | + | |
| fixation of $CO_2$ | + | | | | |
| $NO_3$ as nitrogen source | + | + | | | + |
| temperature opt. °C. | 37° | 30° | 30° | | 37° |
| growth on amino acids | − | | | | ± |
| methanol as C source | + | | + | + | + |
| methane as C source | + | + | + | + | + |
| ethanol as C source | − | − | − | + | |
| hexulose phosphate pathway | + | + | + | + | + |
| serine pathway | − | | | | |
| formaldehyde | | | | | |
| formiate | | | | | |
| trimethylamide | + | | | | |
| dimethylamide | | | | | |
| G + C (%) | | 50–54 | 50–54 | 50–54 | 62,5 |

| | Methylosinus methylocystis | Ps. methanolica | Pseudomonas AM 1 | Ps. methylotropha | Methylomonas methanica |
|---|---|---|---|---|---|
| motility | | | | + | |
| formation of pigments | | | | | ± |
| pHBS | | + | + | − | |
| fixation of $N_2$ | | | | | |
| fixation of $CO_2$ | | | | | |
| $NO_3$ as nitrogen source | | | | | |
| temperture opt. °C. | | | | | |
| growth on amino acids | | | | | |
| methanol as C source | | + | + | + | + |
| methane as C source | | − | − | − | + |
| ethanol as C source | | | + | − | − |
| hexulose phosphate pathway | | | | | |
| serine pathway | + | | | | |
| formaldehyde | | | | − | − |
| formiate | | | | − | − |
| trimethylamide | | | | − | − |
| dimethylamide | | | | | |

| | | | |
|---|---|---|---|
| G + C (%) | 62,5 | 54 | 52,1 |

Table 1-continued

The following examples illustrate the invention:

EXAMPLE 1

The strain *Methylomonas clara* FH-B-5460 ATCC 31226 is cultivated on slants containing

| 18 g of | gar |
| --- | --- |
| 2.0 ml of | $H_3PO_4$ of 85% strength |
| 3.0 ml of | $NH_4OH$ of 12% strength |
| 0.01 g of | $Na_2HPO_4$ |
| 1.2 g of | $H_2SO_4$ |
| 0.8 g of | $MgSO_4 \cdot 7 H_2D$ |
| 0.03 g of | $FeSO_4 \cdot 7 H_2O$ |
| 10.0 ml of | methanol (added prior to filling the tubes) |
| 1.0 ml of | solution of trace elements, containing $CuSO_3$, $H_3BO_3$, $MnSO_4$, $ZnSO_4$, $Na_2MoO_4$ |
| 1 l of | water |
| pH adjustion prior to sterilization to 6.7. | |

The slants are heated for 30 minutes in an autoclave, to a temperature of 120° C. Thereafter they are inoculated with *Methylomonas clara* and kept at a temperature of 37° C. for a period of 2 days. The cell mass of two of the slants is suspended by means of physiological sodium chloride solution and transferred by inoculation to the next stage.

This stage is a shaken culture (preculture), which is placed in a 2 liter Erlenmeyer flask holding 1 liter of nutrient solution (having the same composition as above, but containing no agar). 3.3 ml of methanol (filtered under sterile conditions) are added thereto. This culture is shaken for three days at a temperature of 37° C. in agigator vessels which have an amplitude of 4 cm, at a speed of 220 rpm. After 24 and 48 hours, respectively, 3.3 ml of methanol are added.

The following stage (main culture) is achieved in a fermenter fed with about 20 liters of nutrient solution (having the same composition as above, but containing no agar). After sterilization for 30 minutes, at a temperature of 120° C., under 1.2 to 1.4 bars, 2 liters of preculture are inoculated into the fermenter. Fermentation in the fermenter equipped with flat paddle mixers, an airing ring and three baffles is carried out under the following conditions:

| temperature | 37° C. | |
| --- | --- | --- |
| aeration | 10 liters/minute | 0.5 vvm |
| pressure | 0.2 bars | |
| number of revolutions per minute | 500 | |
| pH | 6.6 | |

20 ml of ethanol are added and further amounts of 20 ml are added each time when the $CO_2$ release of the cells decreases. The methanol concentration amounts only to at most 0.1% by volume thereby.

After 22 hours the 20 liters of culture suspension of the main culture are transferred by inoculation to a prefermenter having a capacity of 200 liters. This fermenter is equipped and is treated in the same way as the main culture. Fermentation is carried out under the following conditions:

| temperature | 37° C. | |
| --- | --- | --- |
| aeration | 6 to 8 m³/h | 0.5 to 0.75 vvm |
| pressure | 0.2 bars | |
| rpm | 380 | |
| pH | 6.7 | |

The pH is maintained in a range of from 6.7 to 6.8 by means of sterile ammonium hydroxide of 10% strength. The methanol supply is controlled by measuring the methanol concentration in the waste air by means of a flame ionization detector, each time, when the methanol concentration falls below 50 ppm, further quantities of methanol are added.

A concentration of methanol in the waste air of 60 vpm corresponds to a concentration of methanol in the solution of 0.22%.

After 20 hours of fermentation a main fermenter is inoculated with 200 liters of culture suspension from the prefermenter; it contains 2000 liters of nutrient solution and works under the following conditions:

| temperature | 37° C. | |
| --- | --- | --- |
| aeration | 60 to 80 m³/h | 0.5 to 0.75 vvm |
| pressure | 0.2 bars | |
| rpm | 170 | |
| pH | 6.7 | |

The methanol feed is carried out in the manner described for the 200 liter prefermenter. The methanol concentration in the nutrient solution is in the range of from 50 to 80 ppm. The cell mass is worked up after a fermentation period of 22 hours. To do this, the pH of the culture suspension is brought to a value of 4.0 by the addition of dilute sulfuric acid and the cell mass is separated by centrifugation in separators at a speed of 400 rpm. Alternatively it may be separated by centrifugation at a pH of from 6.5 to 6.8. The separated cell mass (moisture content 80%) is washed with water and then dried to a dry content of 25% in the separator. Thereafter the cell mass is dried in a spray dryer at an entrance temperature of from 120° to 150° C. The powder obtained still has a moisture content of from 1.5 to 3.5% and contains 85% of crude protein (N×6.25)
74% of amino acids, comprising about 50% of essential amino acids
8 to 12% of nucleic acids
6 to 8% of crude fat
5 to 6% of crude ash
(the percentages are to be understood as percentages by weight).

EXAMPLE 2

The strain *Methylomonas clara* FH-B-5460 ATCC 31226 is cultivated as in Example 1.

The main fermenter is intended for use in continuous fermentation and has a capacity of 3000 liters. It is permanently aerated and works under the following conditions:

| temperature | 37° C. | |
| --- | --- | --- |
| aeration | 80 Nm³/h | 0.67 vvm |
| pressure | 0.1 bar | |

| | |
|---|---|
| rpm | 390 |
| pH | 6.8 |

The main fermenter contains 2000 liters of nutrient solution (of the same composition as in Example 1, but containing no agar) and is inoculated with 200 liters of culture suspension of the prefermenter. The methanol concentration is measured in the manner described hereinbefore and controlled by the addition of methanol/water at a ratio by volume of 40:60 to maintain an average free conentration of methanol in the range of from 10 to 50 ppm in the nutrient solution.

Continuous operation is started, when 7 to 10 kg of cell mass/1 have been produced.

The nutrient medium is added at a throughput rate of 0.25/h. This rate is increased to 0.33/h, which corresponds to about 650 l/h, after a period of about 12 hours. The mean free concentration of methanol is maintained between 10 and 20 ppm. The corresponding quantity of nutrient medium, on which bacteria have grown, is drawn off, kept for a period of 1 to 2 hours in an intermediate placed vessel without adding methanol and is then submitted to the cell separation and drying processes as described in Example 1.

The cell mass obtained has a moisture content of from 2 to 4% and contains

81% of curde protein ($N \times 6.25$)
70% of amino acids, among which about 50% of essential amino acids
8 to 10% of nucleic acids
5 to 10% of crude fat
5 to 10% of crude ash

What is claimed is:

1. A method for preparing a biomass which comprises cultivating a strain of the species *Methylmonas clara* ATCC 31226 under aerobic conditions in a nutrient medium containing a nitrogen source, essential mineral salts, and methanol at a concentration between 5 ppm and 150 ppm, by weight of the nutrient medium, as the sole carbon source.

2. A method as in claim 1 which is performed continuously and wherein the concentration of methanol is between 5 ppm and 30 ppm.

* * * * *